(12) United States Patent
Bottlinger, Jr. et al.

(10) Patent No.: US 8,479,557 B2
(45) Date of Patent: Jul. 9, 2013

(54) SHOCK SIMULATION METHOD AND APPARATUS

(75) Inventors: Esteen Bottlinger, Jr., Chandler, AZ (US); Patrick Grosserode, Chandler, AZ (US); Krzysztof Zbigniew Pennar, Chandler, AZ (US); Gary Ronald Burnside, Phoenix, AZ (US)

(73) Assignee: Orbital Sciences Corporation, Dulles, VA (US)

( * ) Notice: Subject to any disclaimer, the term of this patent is extended or adjusted under 35 U.S.C. 154(b) by 267 days.

(21) Appl. No.: 12/874,211

(22) Filed: Sep. 1, 2010

(65) Prior Publication Data

US 2012/0047989 A1    Mar. 1, 2012

(51) Int. Cl.
*G01M 7/00* (2006.01)
(52) U.S. Cl.
USPC ............................... 73/12.08; 73/12.01
(58) Field of Classification Search
USPC .................... 73/12.01, 12.08, 12.09
See application file for complete search history.

(56) References Cited

U.S. PATENT DOCUMENTS

| | | | | |
|---|---|---|---|---|
| 3,670,559 A | * | 6/1972 | Bement | 73/35.15 |
| 5,003,811 A | * | 4/1991 | Shannon et al. | 73/12.14 |
| 5,565,626 A | * | 10/1996 | Davie | 73/579 |
| 6,634,209 B1 | * | 10/2003 | Kastendieck et al. | 73/12.07 |
| 7,446,542 B2 | * | 11/2008 | Zaykova-Feldman et al. | 324/750.01 |
| 7,464,597 B1 | * | 12/2008 | Lee et al. | 73/663 |
| 7,878,042 B2 | * | 2/2011 | Talley et al. | 73/12.06 |
| 8,011,928 B1 | * | 9/2011 | Schaeffer et al. | 434/11 |
| 8,105,087 B2 | * | 1/2012 | Valentini | 434/11 |

* cited by examiner

*Primary Examiner* — Max Noori
(74) *Attorney, Agent, or Firm* — Ropes & Gray LLP

(57) ABSTRACT

A shock simulation test apparatus and method utilize a test plate and formed explosive charges to sever or penetrate one or more portions of a suspended test plate in order to subject any attached test item(s) to a realistic pyroshock stimulus. One or more shock measurement sensors, such as accelerometers, may be attached to the test plate or the test item(s) to measure the response to this shock stimulus. The apparatus and method is flexible in that many different scenarios can be simulated from different test plate materials, charge sizes and types. This method replicates actual end-use source shock environments typical in aerospace applications, but can be extended to any industry having a pyroshock environment and test requirement.

32 Claims, 6 Drawing Sheets

SHOCK SIMULATION METHOD AND APPARATUS

BACKGROUND OF THE INVENTION

The invention relates generally to shock simulation apparatus and methods for testing any industry hardware, component(s) or subsystem(s), electronic or otherwise. More particularly, the invention relates to utilizing formed explosive charges mounted on a test plate which completely or partially sever a portion of the plate, or penetrate a part of the plate, to simulate pyroshock test conditions, which are efficient, repeatable and with less damage to the test plate.

Components and subsystems of larger systems exposed to environments which are generated by explosives or explosive events are often subjected to pyroshock testing to prove they can survive in the actual application. Components typical of aerospace systems are often subjected to pyroshock events during powered flight or field deployment. Explosive devices such as linear shaped charges, flexible linear shaped charges, or mild detonating fuse, may produce these shock events. Additionally, components may also be subjected to complex shocks that travel through multiple structures as a result of an explosive event. As a result, system components and subsystems must be qualified for these environments which often include required margins, which typically are 6 dB, or double the actual environment. Due to the high cost and complexity of most aerospace systems, component qualification using the actual pyroshock environment on full scale assemblies is not practical, and would not produce the required margins. For this reason, laboratory simulations of shock environments are conducted on individual components and subassemblies. Over the years, the ability to measure the actual shock environment, both in flight and during ground tests, has become increasingly better as analytical measurement technologies have improved. Because of this, as well as having to include required margins, the aerospace industry demands improved shock testing capability. This has driven test labs to provide increasingly higher shock magnitudes with more precision, predictability and repeatability.

Traditionally, pyroshock simulation has been performed using varying lengths (typically 5-50 feet) of detonating cord taped in place and initiated with a blasting cap. For example, in one known system, a smaller plate, or 'shelf', is attached (typically welded) to the larger test plate which is typically 0.5 inch to 1 inch thick. One or more test item(s) is mounted on the shelf and an explosive charge is affixed on the back side of the test plate. Elastic cords or chains suspend this entire system vertically i.e., so that the primary plane of the test plate is vertical. Detonation of the explosives subjects the test item to the resulting shock stimulus, which are measured by one or more accelerometers mounted either directly on the test plate or on the shelf or on the test item(s). In another known system, a test plate is suspended horizontally i.e., so that it's primary plane is horizontal, and one or more test item(s) are mounted directly on this test plate. The explosive is affixed either on the bottom side of the test plate or along the perimeter edge of the test plate. The test item is subjected to the shock stimulus resulting from detonation of the explosive charge, which is measured by accelerometers mounted on the plate or the test item(s).

An increasing number of applications within the aerospace industry are requiring shock simulations to meet shock magnitudes of 30,000 to 60,000 g's, or more. Using the above-described traditional methods to generate shocks of this magnitude can cause large deformations to the test plate and subsequent damage to the test item(s) and their mounting configurations (e.g. shelves) that interface to the test plate. The damage to the test plate can also disrupt the plate's mechanical properties, which complicates test repeatability within the specified tolerance bands. Consequently, test plates have to be frequently replaced (or repaired) and the test apparatus must be re-calibrated prior to each subsequent use, which increases cost and can cause schedule delays.

Additionally, the test facility may be only able to withstand a certain level of net explosive weight (NEW) that is fired to generate each shock. In one of the previous examples, in order to generate a 30,000 g minimum shock magnitude, 40 ft of 50 grains/foot (gr/ft) detonating cord was used. This results in firing a little over a quarter pound of explosives (129 grams) for each shock. For explosive weights of this magnitude to be repeatedly fired, structural capabilities, safety, and survivability of the facility must be strongly considered.

SUMMARY OF THE INVENTION

In order to overcome these and other shortcomings, one aspect of the invention relates to utilizing formed explosive charges to completely or partially sever or penetrate a small portion of a test plate. This results in a system capable of high shock magnitudes, being easily reconfigured for repeat testing, and capable of simulating a varying range of shock conditions with relatively little NEW per shock.

In one embodiment, the test plate may be made out of an aluminum alloy. The test plate may be flat and of rectangular shape. One or more shock measurement sensors or accelerometers, one or more test items, and one or more formed explosive charges may be mounted or attached to the test plate. The explosive charges may be linear shaped charges (LSC), conical shaped charges (CSC), etc. The explosive charges may be mounted to the test plate on the opposite end from the test item, such that detonating the explosives results in one or more portion(s) of the test plate being completely or partially severed or penetrated. The severing or penetrating of the test plate results in localized, minimal, plate deformation, and allows for mounting the next explosive charge repeatedly in this general area of the plate. Penetrating, as used herein with respect to a test plate, refers to cutting into, but not entirely through, the test plate The resulting shock stimulus will travel through the test plate and into the test item. Multiple explosive charges may be detonated simultaneously to increase the shock magnitude if required. The process may be repeated by mounting additional explosives for subsequent tests as described and this process can be repeated until all desired pyroshock simulations have been conducted.

In one embodiment, the test plate may be curved to simulate the shape or geometry of an actual component or subsystem (e.g., a missile assembly or rocket motor structure) to which the test item would mount in the actual application. Similar to the previous embodiment, a portion of the plate (possibly from one or both ends) may be severed repeatedly until all pyroshock simulations are complete. The magnitude of shock experienced by the test item may also be controlled by varying the mounting location and/or orientation of the test item. For example, the test item may be subjected to a higher shock if it is mounted directly on the test plate than if it is mounted on, for example, a shelf attached to the test plate.

In one embodiment, the charge type, mounting location, size, standoff, "effective length" (the length of the resulting cut as measured on the plate) and NEW of the explosive charges may be selected based on the thickness and/or the material properties of the test plate. For example, severing a test plate that is 0.500 inches thick may require more NEW than severing a test plate that is 0.250 inches thick. Additionally, these parameters may also be varied to "tune" for a desired level or magnitude of the resulting shock stimulus. For example, an effective length of 20 inches of 25 gr/ft LSC may be utilized to generate an approximate 40,000 g peak shock magnitude.

BRIEF DESCRIPTION OF THE DRAWINGS

The above and other features of the present invention, its nature and various advantages will be more apparent upon consideration of the following detailed description, taken in conjunction with the accompanying drawings, in which like reference characters represent like parts throughout and in which.

DETAILED DESCRIPTION

To provide an overall understanding of the invention, certain illustrative embodiments will now be described, including a method and apparatus for simulating shock. However, it will be understood by one of ordinary skill in the art that the systems and methods described herein may be adapted and modified as is appropriate for the application being addressed and that the systems and methods described herein may be employed in other suitable applications, and that such other additions and modifications will not depart from the scope hereof.

Figure 1A:
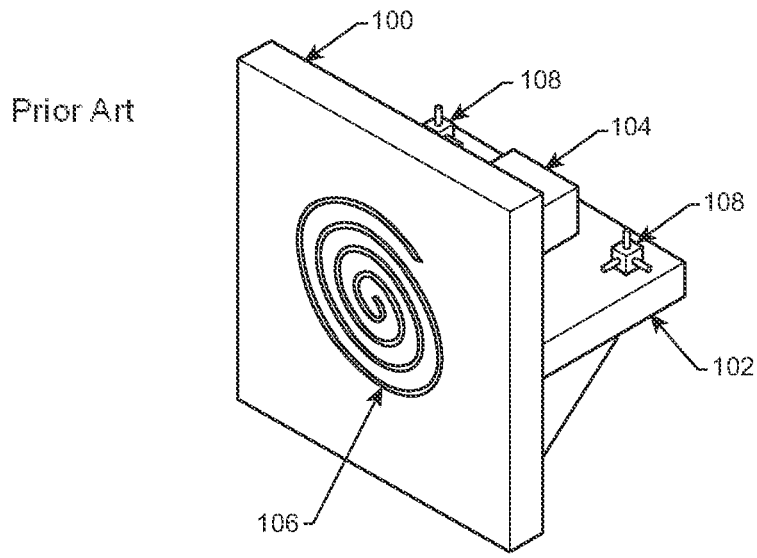
FIGS. 1A-1B are diagrams illustrating prior art systems of simulating shock.
Figure 1B:
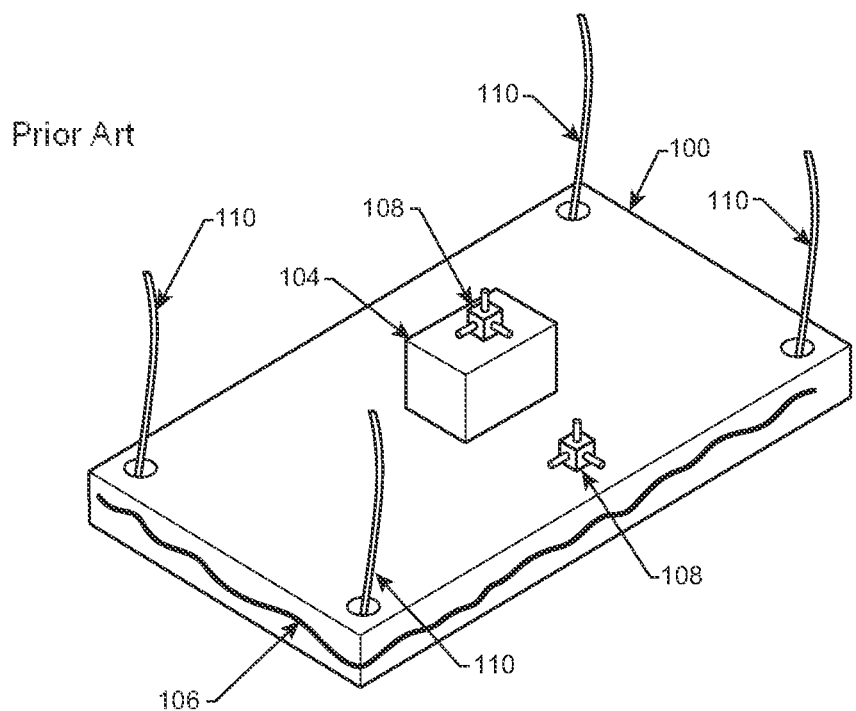

FIGS. 1A-1B show some of the prior art systems as discussed in the background section that have been traditionally used for simulating shock. As shown in FIG. 1A, mounting shelf 102 is attached to plate 100 which is typically 0.5 inch to 1 inch thick. A test item 104 is mounted on shelf 102 and explosive 106 is mounted on the opposite side of plate 100. Explosive 106 is typically detonating cord. Detonation of explosive 106 subjects test item 104 to the resulting shock stimulus, which is measured by one or more sensors 108 mounted on plate 100 or on shelf 102. FIG. 1B shows another prior art system in which plate 100 is hung horizontally by elastic cords 110 and test item 104 is mounted directly on plate 100. Explosive 106 is mounted either on the bottom side (not shown) of plate 100 or along the perimeter edge of plate 100. Similar to the system of FIG. 1A, test item 104 is subjected to shock stimulus resulting from detonation of explosive 106, which is measured by sensors 108.

Figures 2A, 2B:
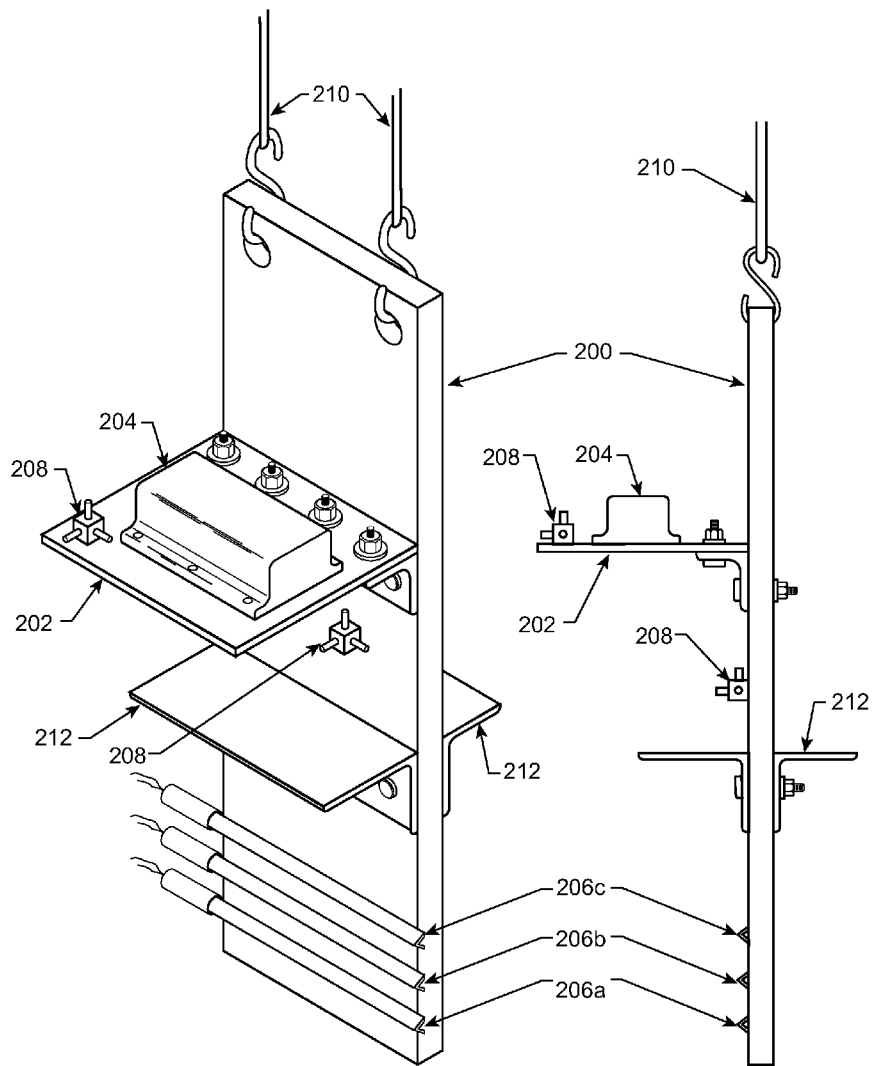
FIGS. 2A-2B are perspective views of a system of simulating shock, according to an illustrative embodiment of the invention.
Figure 2C:
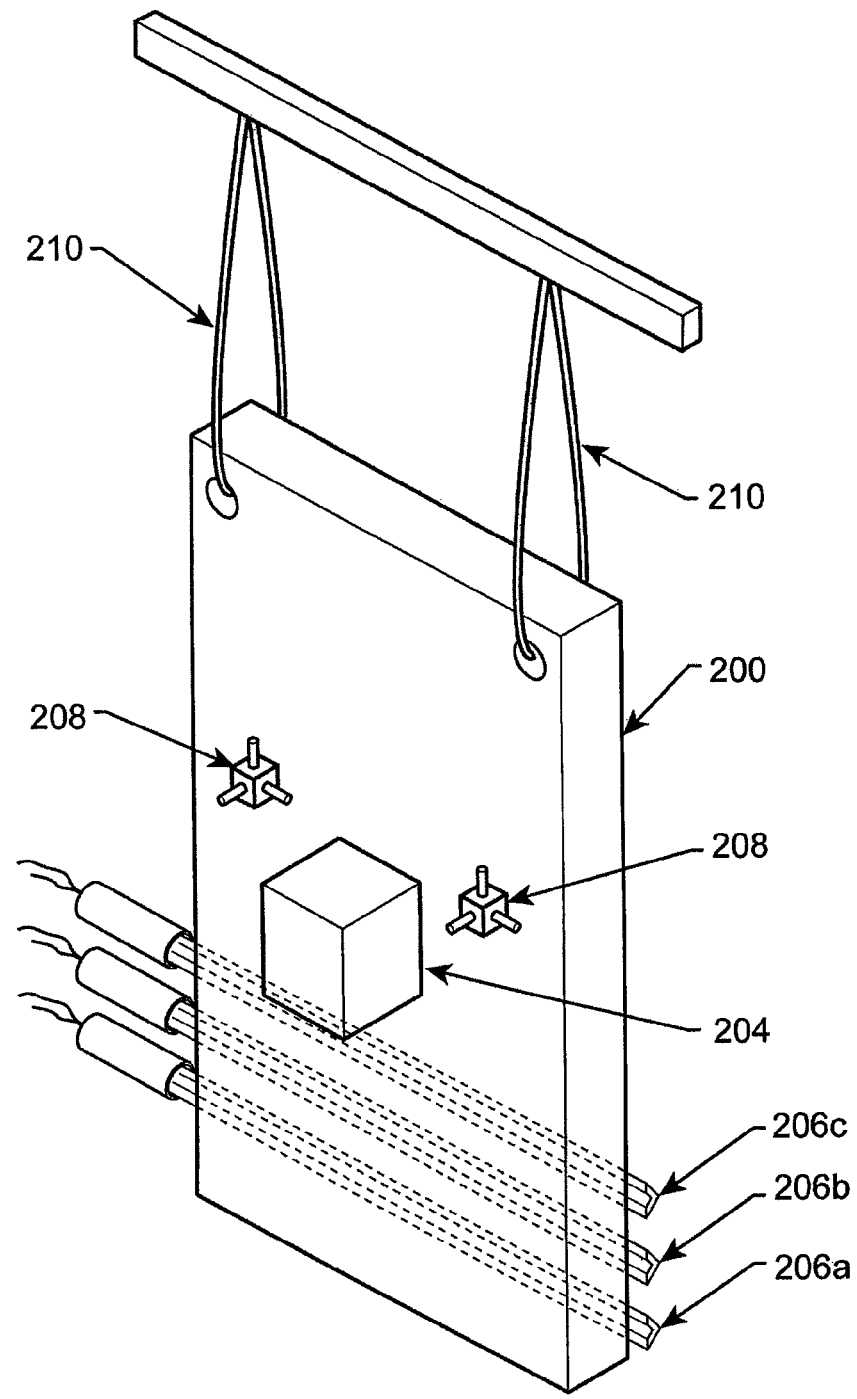
FIG. 2C is a diagram illustrating a system of simulating shock, according to an illustrative embodiment of the invention.

FIGS. 2A-2C show a system for simulating shock in accordance with an exemplary embodiment of the invention. Test plate 200 is suspended vertically using elastic cords 210. In alternate embodiments, the test plate may be suspended horizontally or in any other orientation using cables, chains, rope, wires, etc. Additionally, in alternate embodiments, the test plate may be fixed on one or more sides using for example, welds or mechanical fasteners, such as nuts, bolts, screws, etc. A shelf 202, as shown in FIGS. 2A and 2B may be fastened to test plate 200. Shelf 202 may be welded to gussets or fastened using mechanical fasteners. The test plate may be of any thickness, and the thickness is selected based on the shock requirements of the test being conducted, and based on the characteristics of the explosive being used in the test. However, the test plate is preferably about 0.040 inches to about 1.0 inches thick. Test plate 200 is made out of an aluminum alloy. Alternatively, the test plate may be made from any other material, and the material may be selected based on the cost, availability, properties related to shockwave propagation, or properties with respect to an end-use (i.e., non testing) application. For example, the test plate may be made from a graphite-epoxy composite material to more accurately simulate end use applications.

In the embodiment of FIGS. 2A and 2B, test item 204 and sensors 208 are mounted on shelf 202. In the embodiment shown in FIG. 2C, test item 204, sensors 208 and explosive(s) 206 are mounted directly to test plate 200. Test item 204, sensors 208 and/or explosive(s) 206 may be mounted to test plate 200 using for example, adhesive, tape, screws, nuts and bolts, etc. The mounting location and/or orientation of test item(s) may be determined based on the shock requirement. For example, mounting a test item closer to explosive(s) may result in the test item being subjected to a shock stimulus of greater magnitude than mounting the test item further away from explosive(s). Explosive(s) may also be mounted anywhere on the test plate and at any orientation.

In the exemplary embodiments of FIGS. 2A-2C, explosive(s) 206 are linear shaped charges (LSC). Shaped charges are explosive charges which are configured to focus their explosive energy in a particular area or region. A typical shaped charge includes a metal liner surrounded by an explosive. In LSCs the liner has a V-shaped or chevron profile, and in conical shaped charges (CSC) the liner has an inverted cone shape. The type, amount, mounting location, mounting configuration, and number of explosives may be selected based on the shock requirements and/or the thickness and material properties of the test plate. For example, if the explosive is LSC, the length and grain size of LSC is adjusted to accurately "tune" for a desired level or magnitude of the resulting shock stimulus. In one embodiment, 20 inches of 25 gr/ft LSC has been utilized to generate an approximately 40,000 g peak shock magnitude. To increase the magnitude, another embodiment may use 20 inches of 40 gr/ft LSC to sever a thicker plate. A number of other variables may be adjusted to "tune" the plate excitation such that shock response at the test item meets the desired requirements. For example, such variables relative to the test plate include type, size, shape, material, and thickness. Such variables relative to the explosive charge include charge type, size, standoff, "effective length", and NEW. Such variables relative to the test item include mass, size, shape and location on the test plate relative to the charge.

Margin is typically required to demonstrate survivability of the test item beyond expected environments. In alternate embodiments, sensors 208 may not be necessary if shock simulation data from prior tests or calibrations is available. For example, consider a component being tested which needs to withstand a 10,000 g shock. The customer desires additional margin and requests that the component be subjected to a 25,000 g shock. If a shock simulation test was previously conducted using a 0.5 inch thick test plate and 25 gr/ft LSC of a particular length and a particular arrangement to generate a 25,000 g shock, then the component can be tested on a 0.5 inch thick test plate using the same type, amount and arrangement of explosive as the previous simulation test without the need for any shock measurement sensor(s). That is, the shock imparted by the methodology disclosed herein is sufficiently predictable that one can assume repeated detonation conditions will yield consistent levels of shock.

Additionally, explosives may be arranged as shown in FIGS. 2A-2C to allow for repeat testing. In accordance with the exemplary embodiments shown in FIGS. 2A-2C, explosive 206a is detonated first, which results in a portion of test plate 200 being completely severed. Subsequently, explosive 206b is detonated which results in another portion of test plate 200 being severed. Finally, explosive 206c is detonated, which severs yet another portion of test plate 200. This can continue until the number of shock simulations required for the test are achieved. Shock stimulus resulting from the point of detonation may travel through test plate 200 to test item 204. Sensors 208 measure the shock stimulus resulting from each severing or penetration of test plate 200. Sensors 208 may be accelerometers or any other type of shock measurement devices for measuring the induced shock. It should be noted that although test plate 200 shown in FIGS. 2A-2C is flat and rectangular in shape, test plate 200 may be of any size, shape and/or form (e.g., curved). The size, shape and/or form of the plate may be chosen to enable a better simulation of the actual article and test item which allows for actual mounting interfaces to be replicated. In accordance with the embodiment of FIGS. 2A-2B, one or more shields 212 may be mounted to the test plate to protect the test item as well as any instrumentation wires or cables (e.g., from the sensor(s) and/or test item(s)) or any other items mounted to the test plate from shrapnel, debris and/or flame front resulting from detonation of the explosive charge(s). The shield(s) may be made from any material capable of shielding the wires, cables, or test item(s).

Figure 3:
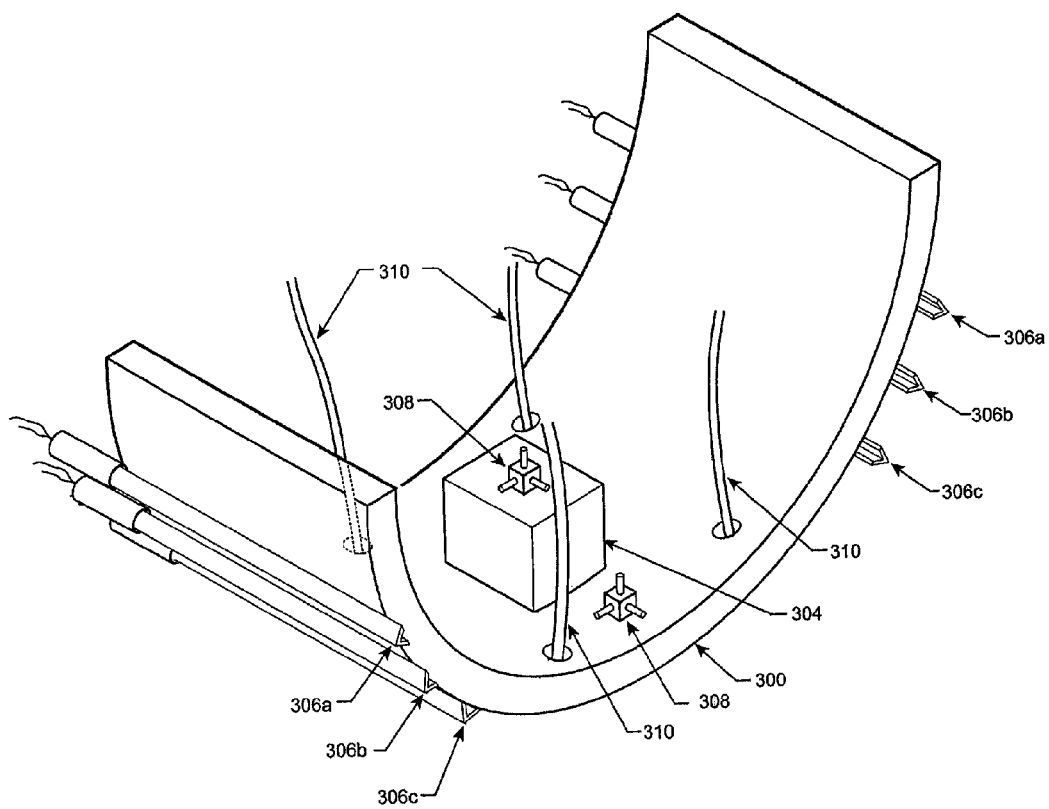
FIG. 3 is a diagram illustrating a system of simulating shock, according to another illustrative embodiment of the invention.

In the exemplary embodiment of FIG. 3, test plate 300 is curved and suspended using elastic cords 310. The curvature of test plate 300 may be selected to replicate the actual application and test item mounting interfaces. In accordance with an exemplary embodiment of the invention, multiple explosives may be used to amplify the magnitude of the shock stimulus experienced by the test item. For example, explosives 306a-306c are mounted as shown in FIG. 3. In one embodiment, both explosives 306a on either side of test plate 300 may be detonated substantially simultaneously such that the initial shockwaves from each detonation arrive at the test item 304 substantially simultaneously. Similarly, both explosives 306b on either side of test plate 300 may be detonated substantially simultaneously in a subsequent test such that the initial shockwaves from each detonation arrive at the test item 304 substantially simultaneously. To repeat the test a third time, both explosives 306c on either side of test plate 300 may be detonated substantially simultaneously in a similar fashion. Sensors 308 measure the shock stimulus resulting from each severing or penetration of test plate 300. In accordance with the embodiment of FIG. 3, one or more shields (not shown) may be mounted to the test plate to protect the test item as well as any instrumentation wires or cables (e.g., from the sensor(s) and/or test item(s)) or any other items mounted to the test plate from shrapnel, debris and/or flame front resulting from detonation of the explosive charge(s). The shield(s) may be made from any material capable of shielding the wires, cables or test item(s). Similar to the embodiments of FIGS. 2A-2C, the embodiment of FIG. 3 also provides the ability to accurately "tune" or vary the level or magnitude of the shock stimulus to meet customer requirements which may include added margins.

In the above described embodiments, the thickness of the test plate is preferably about 0.040 inches to about 1.0 inch. However the test plate may be of any thickness, and the thickness of the test plate may be determined based on characteristics of the explosives being used. For example, the thickness of the test plate may be determined based on the material cutting capabilities of the explosive to ensure proper transfer of shock stimulus. For example, if the material is aluminum and is 0.175 inches thick, then 25 gr/ft LSC may be utilized. However, if the material of the plate is composite (e.g., graphite-epoxy), and is 0.175 inches thick, then a higher grain size LSC may be utilized.

In the above described exemplary embodiments, detonation of explosives may result in a portion of the test plate being completely severed, or partially severed or penetrated. In contrast with known shock simulation methods, the shock simulation method in accordance with an embodiment of the invention only causes structural damage to the test plate in the area of detonation. The remainder of the test plate does not suffer significant permanent structural deformation. As a result, the test item does not suffer any significant damage from bending or warping of the test plate. Consequently, any damage sustained by the test item may be solely attributed to the shock stimulus. Therefore, the test plate, test item(s) and measurement sensor(s) may be utilized repeatedly to conduct multiple tests.

Additionally, since explosive events in, for example, aerospace applications typically involve cutting of various structures (e.g., separation joints, fairings deployments, ejection systems, etc.) which may be made from different materials (e.g., metal or graphite-epoxy composite material), the shock generated in the above described embodiments are closely analogous to the shock generated in the test conditions. Given the high cost and complexity of most aerospace systems, component testing using live flight articles and subsystems is not practical. The above described embodiments advantageously allow the testing of components in conditions (materials, thicknesses, explosives, etc) which most closely resemble the actual application conditions and environments.

Figure 4:
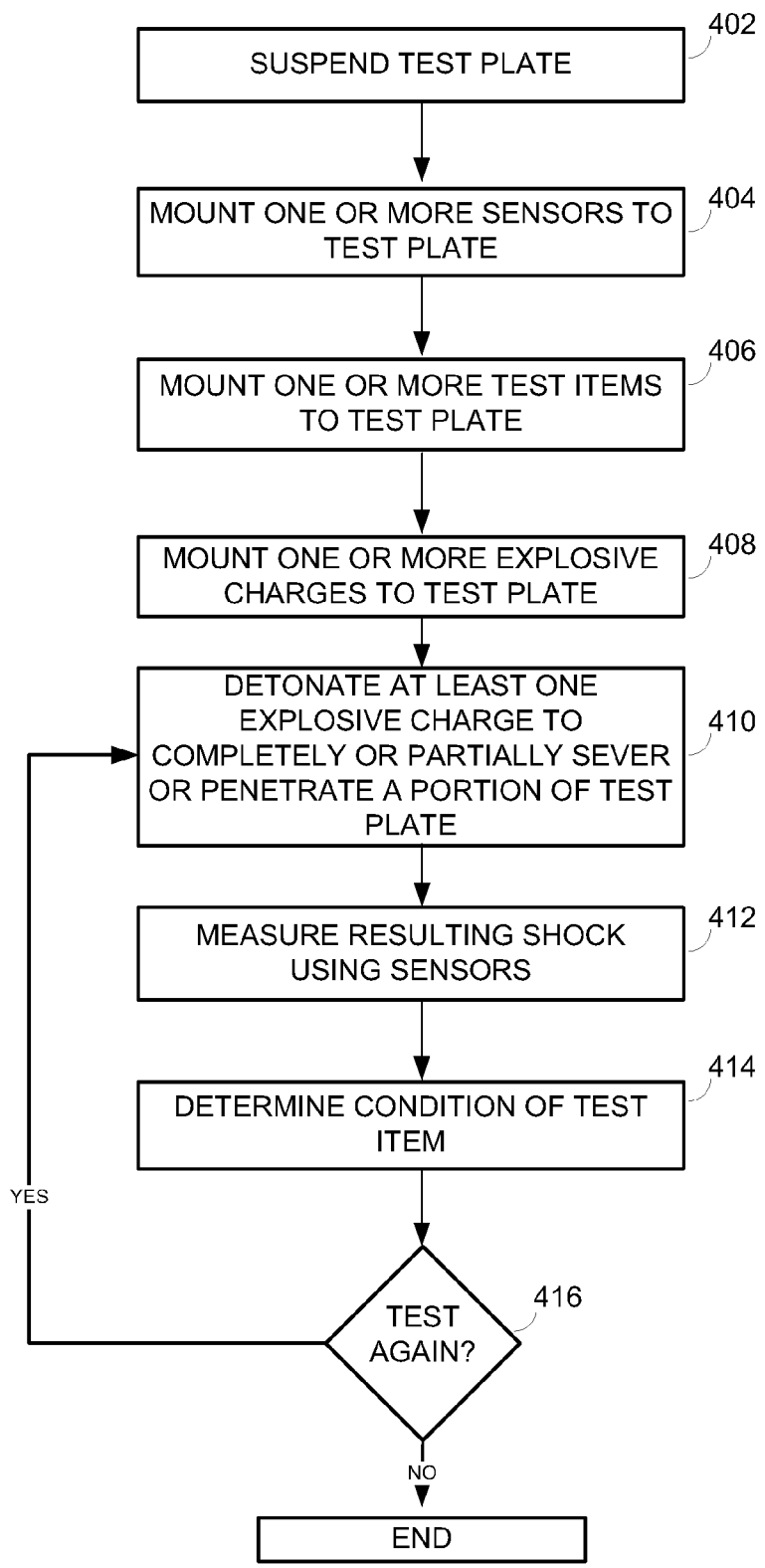
FIG. 4 is a flow chart of an illustrative method of simulating shock using a system similar to that depicted in FIGS. 2 and 3.

FIG. 4 is a flow chart of an illustrative method of testing the shock survivability of a test item, in accordance with an illustrative embodiment of the present invention. The method of FIG. 4 is illustrative in nature and may be applied to test the shock survivability of any component capable of being mounted to a test plate.

In step 402, a test plate is suspended vertically using for example, elastic cords, cables, wires, chains, etc. Alternatively, the test plate may be suspended in any other orientation (e.g., horizontally) or may be fixed on one or more sides. The plate selection may be based on a multitude of parameters, but initial consideration should be based on the available explosive charge to be used, and the actual application. For example, if the charge being used is 25 gr/ft LSC (aluminum sheath with RDX core explosive), an aluminum plate with a thickness up to 0.225" may be sufficient for complete severance. For partial severance or penetration, any aluminum plate thicker than 0.250" may be considered. To measure the shock experienced by the test item, shock measurement sensors are mounted to the test plate (step 404). The sensors may be accelerometers and/or any other shock measurement devices configured to measure the induced shock. One or more test items are mounted to the test plate in step 406. The test item(s) may be mounted directly to the test plate using adhesive, tape, nails, screws, etc. Alternatively, or in addition, the test item(s) may also be mounted to a fixture attached to the test plate (e.g., a shelf) as shown in FIG. 1.

In step 408, one or more formed explosive charges are mounted to the test plate. The type, amount, length, standoff, mounting location, mounting configuration or orientation (mounted to the test plate across the bottom of the plate in a straight line, on an angle, etc.), and number of explosive charges may be selected based on the shock requirements of the test being conducted, and one or more of these variables may be adjusted or modified to "tune" for a desired level or magnitude of the resulting shock. The type, amount, mounting location and mounting configuration of the explosive charges and the thickness of the test plate are selected based on the actual application operating conditions of the test item. The magnitude of shock experienced by the test item may also be controlled by varying the mounting location and/or orientation of the item. For example, the item will be subjected to a higher shock if it is mounted directly on the test plate than if it is mounted on, e.g., a shelf attached to the test plate.

One or more of the explosive charges are detonated to completely or partially sever or penetrate a portion of the test plate in step 410. The shockwave resulting from the severing or penetrating of the test plate travels to the test item(s) through the test plate, and is measured by the sensors and recorded by the data acquisition system (not shown) in step 412. The condition of the test item(s) is determined in step 414. Any damage suffered by the test item(s) may be attributed to the shock resulting from the severing or penetrating of the test plate. This type of testing accurately simulates the actual application of a separation event. Once the test item is deemed to have survived the shock, and if requirements deem it necessary to continue (step 416), another formed charge may be mounted to the test plate. The use of formed charges only locally deforms the test plate so that repeat testing may be conducted using the same calibrated test plate without the need to change out plates and re-calibrate. Testing continues in this fashion until all requirements are met.

In one example, an antenna was tested using the above described method. A curved aluminum (6061 aluminum alloy) test plate was selected. The test plate has a 50" diameter and is 0.187" thick. This plate was then suspended vertically using elastic cords. In this example, 25 gr/ft LSC were mounted to the test plate similar to the configuration shown in FIG. 3. The explosives were mounted with a 0.3" standoff height. To measure the shock experienced by the antenna, accelerometers were mounted to the test plate. The antenna being tested was mounted to the exterior curve of the test plate using mechanical fasteners. Each test comprised of initiating two explosive charges substantially simultaneously using blasting caps, which resulted in complete severance of an approximately one inch portion on either side of the test plate. The shock response resulting from the severing of the plate was recorded using the accelerometers and a data acquisition system (not shown). In this example, the test was repeated three times.

Figure 5:
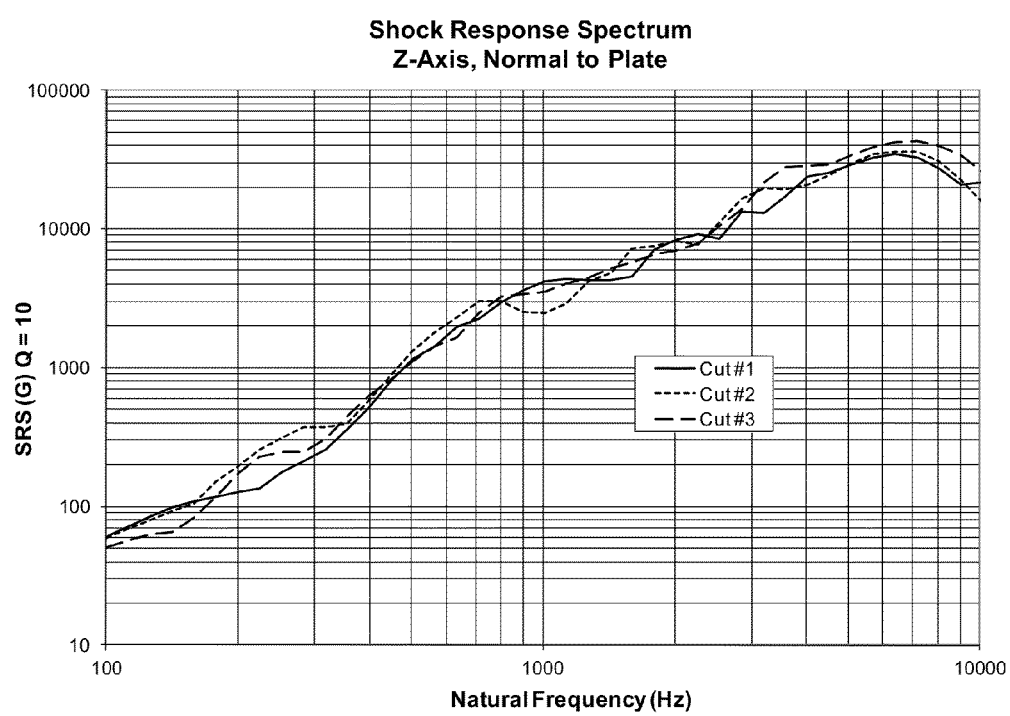
FIG. 5 is a shock response spectrum (SRS) graph of a shock simulation performed using a system similar to that depicted in FIG. 3.

FIG. 5 shows the shock response spectrum (SRS) obtained from the above example in the normal axis, demonstrating repeatability.

The invention may be embodied in other specific forms without departing from the spirit or essential characteristics thereof. The foregoing embodiments are therefore to be considered in all respects illustrative, rather than limiting of the invention. The present invention is limited only by the claims which follow.

What is claimed is:

1. A shock simulation apparatus, comprising:
    a test plate adapted to mount at least one test item; and
    a first shaped charge and a second shaped charge each capable of being mounted to the test plate, the first shaped charge and the second shaped charge arranged to sever or penetrate respective portions of the test plate upon detonation; wherein:
    test item is subjected to shock from detonation of the shaped charge;
    the detonation of the each of the first shaped charge and the second shaped charge causes localized deformation to the test plate in the area of the first shaped charge and the second shaped charge, respectively, and does not cause significant structural deformation to the test plate in the area of the at least one test item; and
    the first shaped charge and the second shaped charge are arranged to allow for repeat testing.

2. The apparatus of claim 1, wherein the first shaped charge and the second shaped charge are selected from the group consisting of a linear shaped charge (LSC), a flexible linear shaped charge (FLSC), and a conical shaped charge (CSC).

3. The apparatus of claim 1, wherein the test plate is comprised of a graphite-epoxy composite material.

4. The apparatus of claim 1, wherein the test plate is curved.

5. The apparatus of claim 1, wherein the first shaped charge is spaced apart from the test item.

6. The apparatus of claim 1, further comprising:
    at least one shock measurement sensor mounted to the test plate for measuring shock induced by detonation of the first shaped charge.

7. The apparatus of claim 1, wherein the first shaped charge induces structural damage to the test plate limited to a detonation area.

8. A method of simulating shock, comprising:
    mounting a first shaped charge to a test plate, said first shaped charge arranged to sever or penetrate a portion of said test plate upon detonation;
    mounting a second shaped charge to the test plate, said second shaped charge arranged to sever or penetrate a portion of said test plate upon detonation, said first shaped charge and said second shaped charge arranged to allow for repeat testing;
    mounting at least one test item to said test plate;
    detonating the first shaped charge to sever or penetrate a portion of the test plate and to subject the test item to shock from detonation of the shaped charge; and
    detonating the second shaped charge to sever or penetrate a portion of the test plate and to subject the test item to shock from detonation of the second shaped charge; wherein
    detonating each of the first shaped charge and the second shaped charge causes localized deformation to the test plate in the area of the first shaped charge and the second shaped charge, respectively, and does not cause significant structural deformation to the test plate in the area of the at least one test item.

9. The method of claim 8, wherein the first shaped charge and the second shaped charge are selected from a group consisting of a linear shaped charge (LSC), a flexible linear shaped charge (FLSC) and a conical shaped charge (CSC).

10. The method of claim 8, further comprising:
    measuring the shock.

11. The method of claim 8, further comprising:
    determining the condition of the test item.

12. The apparatus of claim 1, wherein detonating the first shaped charge does not cause the test plate to bend or warp in the area of the at least one test item.

13. The method of claim 8, wherein shock from detonation of the explosive charges arrives at the test item substantially simultaneously.

14. The method of claim 8 further comprising:
mounting a second test item to the test plate; and
detonating the second shaped charge to sever or penetrate a second portion of the test plate.

15. The method of claim 8, wherein mounting the first shaped charge comprises mounting the first shaped charge apart from the test item.

16. The method of claim 8, further comprising:
selecting the thickness of the test plate based on grain size of the first shaped charge.

17. The method of claim 8, further comprising:
mounting at least one shock measurement sensor to said test plate for measuring shock induced by detonation of the first shaped charge.

18. The method of claim 8, further comprising:
selecting the type and arrangement of the first shaped charge and the second shaped charge and the thickness of the test plate to simulate end-use operating conditions experienced by the test item.

19. The method of claim 8, wherein mounting the first shaped charge comprises arranging the first shaped charge to confine structural damage to the test plate within a detonation area.

20. A method of testing a test item's ability to withstand shock, comprising:
detonating a first shaped charge mounted to a test plate to sever or penetrate a first portion of the test plate and impart shock into the test item, the test item being mounted to the test plate;
detonating a second shaped charge mounted to the test plate to sever or penetrate a second portion of the test plate and impart shock into the test item, wherein the first shaped charge and the second shaped charge are arranged to allow for repeat testing; and
determining the condition of the test item; wherein
the detonation of each of the first shaped charge and the second shaped charge causes localized deformation to the test plate in the area of the first shaped charge and the second shaped charge, respectively, and does not cause significant structural deformation to the test plate in the area of the at least one test item.

21. The method of claim 20, further comprising:
measuring the shock.

22. The method of claim 20, further comprising:
detonating the second shaped charge to sever or penetrate the second portion of the test plate to determine the test item's ability to withstand multiple detonations.

23. The method of claim 22, wherein shock from detonation of the shaped charges arrives at the test item substantially simultaneously.

24. The method of claim 20, further comprising:
selecting the type and arrangement of the first shaped charge and the second shaped charge and the thickness of the test plate to simulate actual operating conditions experienced by the test item.

25. The method of claim 20, further comprising:
arranging the first shaped charge to confine structural damage to the test plate within a detonation area.

26. The apparatus of claim 1, wherein detonation of the first shaped charge does not cause significant structural deformation to the test plate in the area of the second shaped charge.

27. The apparatus of claim 1, wherein the first shaped charge and the second shaped charge are arranged such that if they are substantially simultaneously detonated, shockwaves from each detonation arrive at the at least one test item substantially simultaneously.

28. The apparatus of claim 1, wherein the second shaped charge is capable of being mounted to the test plate after the detonation of the first shaped charge.

29. The apparatus of claim 1, wherein the first shaped charge and the second shaped charge are mounted to the test plate before the detonation of either of the first shaped charge or the second shaped charge.

30. The method of claim 8, wherein the test item is a component of an aerospace system, the method further comprising:
selecting the type and arrangement of the first shaped charge and the second shaped charge to simulate in-flight conditions experienced by the test item.

31. The method of claim 8, wherein the second shaped charge is mounted to the test plate after detonating the first shaped charge.

32. The method of claim 8, wherein the second shaped charge is mounted to the test plate before detonating the first shaped charge.

* * * * *